(12) United States Patent
Barry et al.

(10) Patent No.: US 7,906,133 B2
(45) Date of Patent: *Mar. 15, 2011

(54) OPTIMIZED DOSING FOR DRUG COATED STENTS

(75) Inventors: James J. Barry, Marlborough, MA (US); Kalpana R. Kamath, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 979 days.

This patent is subject to a terminal disclaimer.

(21) Appl. No.: 11/127,499

(22) Filed: May 11, 2005

(65) Prior Publication Data

US 2005/0202061 A1 Sep. 15, 2005

Related U.S. Application Data

(63) Continuation of application No. 10/252,848, filed on Sep. 24, 2002, now Pat. No. 6,908,622.

(51) Int. Cl.
*A61F 2/01* (2006.01)
*A61F 2/02* (2006.01)
*A61F 2/82* (2006.01)
*A61F 2/94* (2006.01)
*A61F 2/06* (2006.01)
*A61F 2/92* (2006.01)

(52) U.S. Cl. .......... 424/423; 514/277; 514/449
(58) Field of Classification Search .......... 424/422, 424/423; 514/277, 449
See application file for complete search history.

(56) References Cited

U.S. PATENT DOCUMENTS

| | | |
|---|---|---|
| 4,529,614 A | 7/1985 | Burns |
| 4,535,006 A | 8/1985 | Naunapper et al. |
| RE32,307 E | 12/1986 | Glatt et al. |
| 4,740,207 A | 4/1988 | Kreamer |
| 4,753,652 A | 6/1988 | Langer et al. |
| 4,758,151 A | 7/1988 | Arru et al. |
| 4,768,507 A | 9/1988 | Fischell et al. |
| 4,776,337 A | 10/1988 | Palmaz |
| 4,795,458 A | 1/1989 | Regan |
| 4,888,009 A | 12/1989 | Lederman et al. |
| 5,007,926 A | 4/1991 | Derbyshire |
| 5,019,090 A | 5/1991 | Pinchuk |
| 5,041,100 A | 8/1991 | Rowland et al. |
| 5,053,048 A | 10/1991 | Pinchuk |
| 5,092,877 A | 3/1992 | Pinchuk |
| 5,102,417 A | 4/1992 | Palmaz |
| 5,171,217 A | 12/1992 | March et al. |
| 5,171,812 A | 12/1992 | Domb |
| 5,175,235 A | 12/1992 | Domb et al. |
| 5,192,307 A | 3/1993 | Wall |
| 5,221,698 A | 6/1993 | Amidon et al. |
| 5,226,913 A | 7/1993 | Pinchuk |
| 5,234,456 A | 8/1993 | Silvestrini |
| 5,236,503 A | 8/1993 | Jones |
| 5,240,963 A | 8/1993 | Domb et al. |
| 5,272,012 A | 12/1993 | Opolski |
| 5,282,823 A | 2/1994 | Schwartz et al. |
| 5,304,121 A | 4/1994 | Sahatjian |
| 5,334,201 A | 8/1994 | Cowan |
| 5,342,348 A | 8/1994 | Kaplan |
| 5,342,621 A | 8/1994 | Eury |
| 5,345,933 A | 9/1994 | Peterson et al. |
| 5,380,299 A | 1/1995 | Fearnot et al. |
| 5,383,928 A | 1/1995 | Scott et al. |
| 5,419,760 A | 5/1995 | Narciso, Jr. |
| 5,423,885 A | 6/1995 | Williams |
| 5,429,634 A | 7/1995 | Narciso |
| 5,437,889 A | 8/1995 | Jones |
| 5,439,686 A | 8/1995 | Desai et al. |
| 5,443,458 A | 8/1995 | Eury |
| 5,443,496 A | 8/1995 | Schwartz et al. |
| 5,447,724 A | 9/1995 | Helmus et al. |
| 5,457,113 A | 10/1995 | Cullinan et al. |
| 5,462,937 A | 10/1995 | Cullinan et al. |
| 5,464,450 A | 11/1995 | Buscemi et al. |
| 5,464,650 A | 11/1995 | Berg et al. |
| 5,475,052 A | 12/1995 | Rhee et al. |
| 5,486,191 A | 1/1996 | Pasricha et al. |
| 5,500,013 A | 3/1996 | Buscemi et al. |
| 5,512,055 A | 4/1996 | Domb et al. |
| 5,516,781 A | 5/1996 | Morris et al. |
| 5,527,337 A | 6/1996 | Stack et al. |
| 5,545,208 A | 8/1996 | Wolff et al. |
| 5,545,213 A | 8/1996 | Keogh et al. |

(Continued)

FOREIGN PATENT DOCUMENTS

| | | |
|---|---|---|
| EP | 0832655 A2 | 4/1998 |
| EP | 0850651 A2 | 7/1998 |
| JP | 10052502 A | 2/1998 |
| JP | 10192413 A | 7/1998 |
| JP | 2001514936 T | 9/2001 |
| WO | WO 94/07529 | 4/1994 |
| WO | WO 94/16706 | 8/1994 |
| WO | 99/08729 A1 | 2/1999 |
| WO | 0040278 A1 | 7/2000 |
| WO | 0062830 A2 | 10/2000 |
| WO | 0187374 A1 | 11/2001 |

OTHER PUBLICATIONS

Japan Patent Office, Office Action in related Japanese application No. 2003-537697, mailed May 25, 2009.
Japan Patent Office, Statement of Reference Publication Offering in related Japanese application No. 2003-537697, dated Jun. 4, 2009.

*Primary Examiner* — Fereydoun G Sajjadi
*Assistant Examiner* — Courtney Brown
(74) *Attorney, Agent, or Firm* — Kenyon & Kenyon LLP

(57) ABSTRACT

The inventors have found that both the drug dose and drug release profiles are significant factors for the safety and efficacy of drug coated stents. The inventors have identified optimum dosing and release kinetics for drug coated stents. In particular, the inventors have determined dosing and release kinetics that permit the delivery of the lowest effective drug dosage, thus enhancing patient safety and minimizing any side effects from the drug.

13 Claims, 2 Drawing Sheets

U.S. PATENT DOCUMENTS

| | | |
|---|---|---|
| 5,551,954 A | 9/1996 | Buscemi et al. |
| 5,554,182 A | 9/1996 | Dinh et al. |
| 5,562,922 A | 10/1996 | Lambert |
| 5,571,166 A | 11/1996 | Dinh et al. |
| 5,575,815 A | 11/1996 | Slepian et al. |
| 5,578,075 A | 11/1996 | Dayton |
| 5,588,962 A | 12/1996 | Nicholas et al. |
| 5,591,227 A | 1/1997 | Dinh et al. |
| 5,599,352 A | 2/1997 | Dinh et al. |
| 5,603,694 A | 2/1997 | Brown et al. |
| 5,605,696 A | 2/1997 | Eury et al. |
| 5,607,417 A | 3/1997 | Batich et al. |
| 5,607,475 A | 3/1997 | Cahalan et al. |
| 5,609,629 A | 3/1997 | Fearnot et al. |
| 5,624,411 A | 4/1997 | Tuch |
| 5,653,760 A | 8/1997 | Saffran |
| 5,679,400 A | 10/1997 | Tuch |
| 5,776,184 A | 7/1998 | Tuch |
| 5,824,048 A | 10/1998 | Tuch |
| 5,824,049 A | 10/1998 | Ragheb et al. |
| 5,833,651 A | 11/1998 | Donovan et al. |
| 5,837,008 A | 11/1998 | Berg et al. |
| 5,843,172 A | 12/1998 | Yan |
| 5,851,217 A | 12/1998 | Wolff et al. |
| 5,851,231 A | 12/1998 | Wolff et al. |
| 5,871,535 A | 2/1999 | Wolff et al. |
| 5,873,904 A | 2/1999 | Ragheb et al. |
| 5,879,697 A | 3/1999 | Ding et al. |
| 5,900,246 A | 5/1999 | Lambert |
| 5,977,163 A | 11/1999 | Li et al. |
| 5,981,568 A | 11/1999 | Kunz et al. |
| 5,997,468 A | 12/1999 | Wolff et al. |
| 6,042,875 A * | 3/2000 | Ding et al. .................. 427/2.24 |
| 6,096,070 A | 8/2000 | Ragheb et al. |
| 6,099,561 A | 8/2000 | Alt |
| 6,099,562 A | 8/2000 | Ding et al. |
| 6,120,536 A | 9/2000 | Ding et al. |
| 6,120,847 A | 9/2000 | Yang et al. |
| 6,146,358 A | 11/2000 | Rowe |
| 6,153,252 A * | 11/2000 | Hossainy et al. .............. 427/2.3 |
| 6,187,370 B1 | 2/2001 | Dinh et al. |
| 6,206,915 B1 | 3/2001 | Fagan et al. |
| 6,206,916 B1 | 3/2001 | Furst |
| 6,228,845 B1 | 5/2001 | Donovan et al. |
| 6,273,913 B1 | 8/2001 | Wright et al. |
| 6,299,604 B1 * | 10/2001 | Ragheb et al. ................. 604/265 |
| 6,335,029 B1 | 1/2002 | Kamath et al. |
| 6,355,055 B1 | 3/2002 | Waksman et al. |
| 6,379,382 B1 | 4/2002 | Yang |
| 6,379,691 B1 | 4/2002 | Tedeschi et al. |
| 6,395,326 B1 | 5/2002 | Castro et al. |
| 6,406,754 B2 | 6/2002 | Chappa et al. |
| 6,908,622 B2 * | 6/2005 | Barry et al. .................. 424/423 |
| 2002/0051730 A1 | 5/2002 | Bodnar et al. |
| 2002/0098278 A1 | 7/2002 | Bates et al. |

\* cited by examiner

Wide Dose Range Screening

*Correlation of Dose with vascular response*

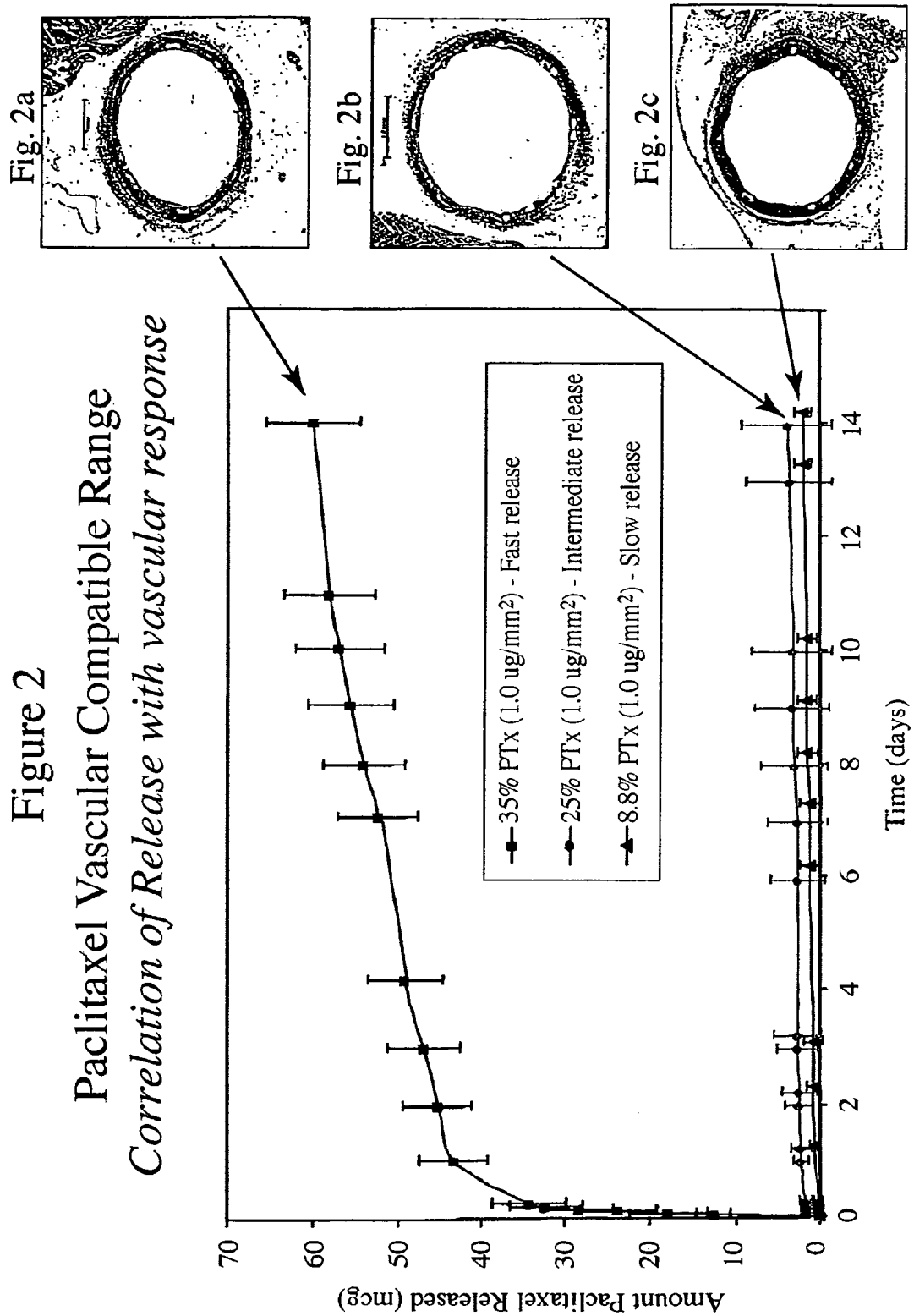

OPTIMIZED DOSING FOR DRUG COATED STENTS

This application is a continuation of application Ser. No. 10/252,848, filed Sep. 24, 2002, now U.S. Pat. No. 6,908,622, the entire contents of which are hereby expressly incorporated by reference in their entirety.

FIELD OF THE INVENTION

The present invention relates to optimized biological responses as a function of dosage and release kinetics of drugs from implantable medical devices.

BACKGROUND OF THE INVENTION

Stents are tubular scaffold structures used to prop open blood vessels and other body lumens. The most widespread use of stents is to open clogged coronary arteries and prevent restenosis. The use of stents coated with therapeutic agents has been proposed to help minimize the possibility of restenosis. For example, stents coated with paclitaxel have been shown to reduce restenosis rates when compared with uncoated stents.

Although a number of drug coated stents have been reported, there has been a lack of published information regarding the optimization of drug dosing and drug release kinetics to address safety and efficacy. There is thus a need to identify, for a given coated stent system, the effective therapeutic window based on the selection of an appropriate drug dose to obtain a desired biological response.

SUMMARY OF THE INVENTION

The inventors have identified preferred drug dosing and drug release profiles for the safety and efficacy of drug coated stents. The embodiments described herein are specific to metallic stents coated with paclitaxel in a polymeric carrier, but the invention is thought to be applicable to stents coated with other drugs, with or without a polymeric carrier.

In one embodiment, the invention includes a drug coated stent comprising a structural member insertable into a body lumen of a patient, and a drug coated onto at least a portion of the said structural member. The drug is released from the stent into the patient for a time period of at least eight days after insertion into the patient.

In another embodiment, the invention includes a drug coated stent, where the drug is released from the stent at a varying rate over time. The rate is preferably maximized between one and three days after insertion into the patient.

In another embodiment, the invention includes a paclitaxel coated stent wherein after ten days following insertion into a patient, only less than about 60 micrograms of paclitaxel is released from the stent.

In another embodiment, the invention includes a paclitaxel coated stent wherein after two days following insertion into a patient, only less than about 10 micrograms of paclitaxel is released from the stent.

In another embodiment, the invention includes a paclitaxel coated stent having a dosage of up to about 2 micrograms per square millimeter of the stent surface area.

In yet another embodiment, the invention includes a paclitaxel coated stent, wherein the paclitaxel is included in a polymer carrier and the weight fraction of the paclitaxel in the polymer carrier is less than about 35 percent.

DESCRIPTION OF THE DRAWINGS

FIG. 2 and FIGS. 2a-2c illustrate the difference in biological response resulting from the difference in release rate from a paclitaxel coated stent.

DETAILED DESCRIPTION OF THE INVENTION

Figure 1:
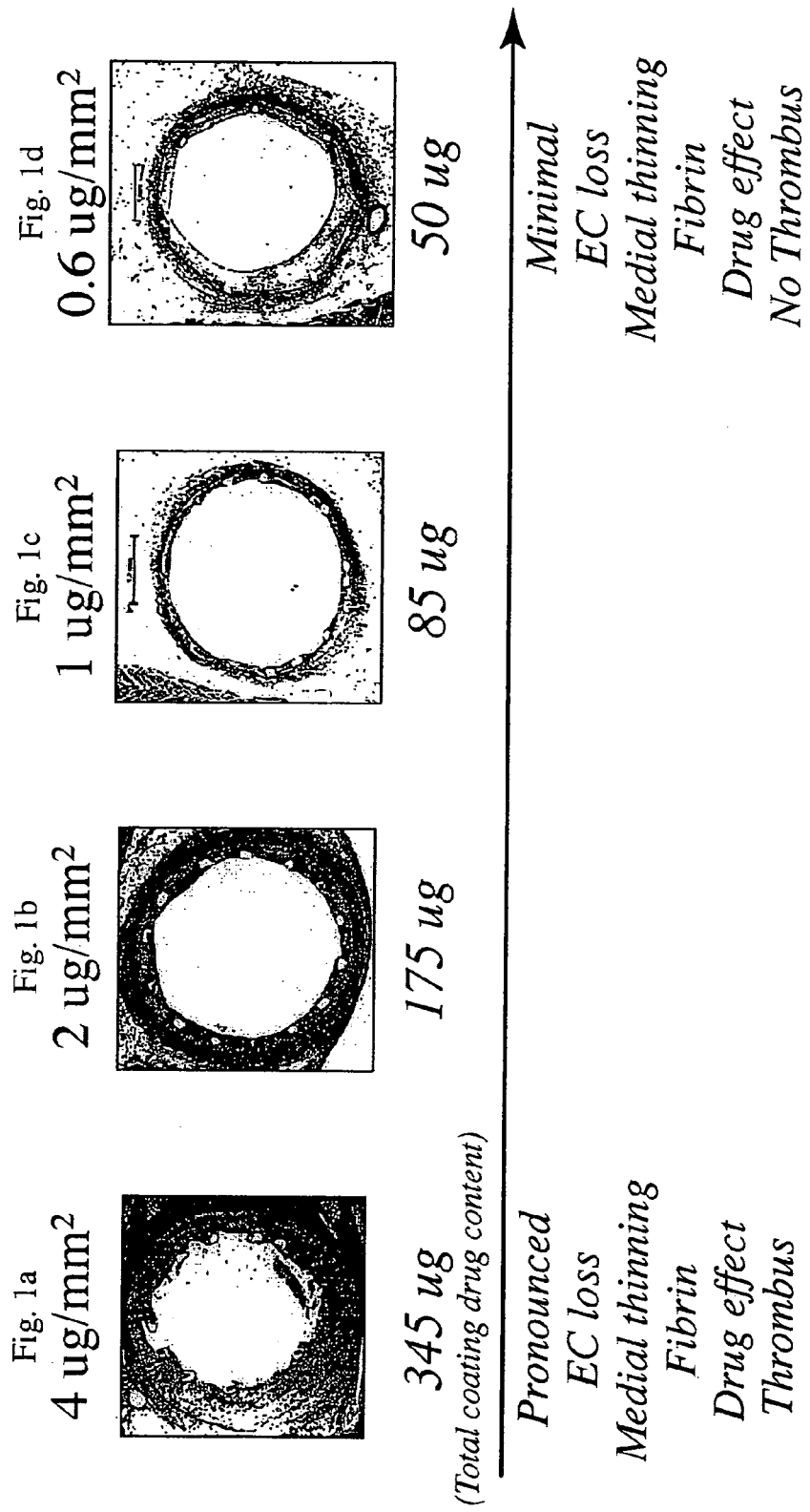
FIG. 1 shows histology results from a porcine dosing study.

The inventors have found that both the drug dose and drug release profiles are significant factors for the safety and efficacy of drug coated stents. The inventors have identified optimum dosing and release kinetics for drug coated stents. In particular, the inventors have determined dosing and release kinetics that permit the delivery of the lowest effective drug dosage, thus enhancing patient safety and minimizing any side effects from the drug.

In a preferred embodiment of the present invention, the drug for coating a stent is paclitaxel. Other drugs that may be useful for treating diseases such as restenosis include known anti-inflammatory, anti-thrombogenic, anti-angiogenic, matrix production inhibitory, anti-migratory, cytostatic, and/or cytotoxic agents. Drugs currently being used or considered as stent coating materials to combat restenosis include paclitaxel, sirolimus, tacrolimus, and everolimus. The present invention is thought to be applicable to any of these restenosis inhibiting drugs.

In another preferred embodiment, the drug paclitaxel is contained in a polymer coating applied to a metallic stent. In certain embodiments, the polymer coating is a styrene-isobutylene based block copolymer, olefin polymer, polyethylene, polypropylene, polyvinyl chloride, polytetrafluoroethylene, fluorinated ethylene propylene copolymer, polyvinyl acetate, polystyrene, poly(ethylene teraphthalate), polyurethane, polyurea, silicone rubbers, polyamides, polycarbonates, polyaldehydes, natural rubbers, polyester copolymers, styrene-butadiene copolymers ethylene vinyl acetate, polyorthoesters, polyiminocarbonates, aliphatic polycarbonates, polycaprolactone (PCL), poly-DL-lactic acid (DL-PLA) or poly-L-lactic acid (L-PLA), lactide, polyphosphazenes, polyethylene oxide or polyethylene terephthalate (PET), polybutylene terephthalate(PBT), PEBAX, Nylon, or polycaprolactone, polyorthoesters, polylactic acids, polyglycolic acids, albumin or combinations of any of the above. In a most preferred embodiment, the polymer is a styrene-based polymer.

Paclitaxel coated metallic stents of various doses were implanted into healthy porcine arteries to determine the effect of dosage on biological response. Dosages used were approximately 4.0, 2.0, 1.0, and 0.6 micrograms per square millimeter of the stent surface area, corresponding to approximate total dosages of 345, 175, 85, and 50 micrograms per stent. The paclitaxel was contained within a styrene-isobutylene based block copolymer applied to the stent struts. As can be seen in FIG. 1a, the highest dose (i.e. 4.0 micrograms/mm$^2$) resulted in a pronounced vessel relaxation, fibrin accumulation, medial thinning, loss of endothelial cells, and possible thrombus formation.

As the dose is decreased, the adverse effects described for the 4.0 micrograms/mm$^2$ dose are minimized. At 2.0, 1.0, and 0.6 micrograms/mm$^2$, there is a corresponding decrease in the effects of paclitaxel, such that endothelial cell loss, medial thinning, fibrin accumulation, and possible thrombus formation are all minimized. Based on these results, the preferred paclitaxel dosage is up to about 2.0 micrograms/mm$^2$, more preferably less than about 1.5 micrograms/mm$^2$, and most preferably up to about 1.0 micrograms/mm$^2$.

In particular embodiments, the dosage is 0.4 to 2.0 micrograms/mm$^2$, 0.7 to 1.5 micrograms/mm$^2$, or 1.0 to 1.3 micrograms/mm². In other embodiments, the dosage is 0.4, 0.5, 0.6, 0.7, 0.8, 0.9, 1.0, 1.1, 1.2, 1.3, 1.4, 1.5, 1.6, 1.7, 1.8, 1.9, or 2.0 micrograms/mm².

Using the 1.0 micrograms/mm² dose as an exemplary embodiment, the effects of release rate were investigated. Metallic stents were coated with paclitaxel in a styrene-isobutylene based block copolymer carrier with the weight percent of paclitaxel in the carrier varying from approximately 8.8 to about 35%. The dose of drug applied to the stents was kept at 1.0 micrograms/mm², and the total drug dose was held constant by varying total coating weight. The results shown in FIG. 2, as determined from in vitro release studies involving an aqueous environment, illustrate that the different weight fractions of paclitaxel in the polymer carrier resulted in different release kinetics.

In particular embodiments, the weight percent of paclitaxel in the carrier or polymer coating is 5% to 35%, 10% to 30%, 15% to 25%, or 18% to 22%.

As can be seen from FIG. 2, there was a direct correlation between drug weight fraction in the carrier and the release rate. For example, the highest weight fraction tested (35%) resulted in the release of approximately 45 micrograms of paclitaxel within two days after implantation. In contrast, the lowest weight fraction tested (8.8%) resulted in the release of only about 2 micrograms of paclitaxel within the same time period. The fastest release rate (FIG. 2a) resulted in noticeable fibrin accumulation, whereas slower rates (FIGS. 2b and 2c) did not result in this effect. It is thus demonstrated that drug release rate, in addition to drug dosing, affects biological response.

Based on these results, a high weight fraction of paclitaxel (35% in a polymer carrier) is acceptable, but a preferred weight fraction of paclitaxel is less than about 35% for a 1.0 micrograms/mm² dosage, more preferably up to about 25%.

Most preferably, dosing of approximately 1.0 micrograms/mm² of paclitaxel in a polymer coating was found to yield superior safety and efficacy. Within this dose, the preferred weight fraction of paclitaxel in this particular polymer carrier is less than about 35%. Such a combination results in the release of less than about 60 micrograms of paclitaxel within ten days after implantation, and less than about 45 micrograms within two days. As the inventors have found that lower doses lead to preferred physiologic responses, it is preferred that the coating system result in the cumulative release of less than about 20 micrograms of paclitaxel ten days after implantation, more preferably less than 15 micrograms, more preferably less than 10 micrograms, more preferably less than 8 micrograms, more preferably less than 6 micrograms, and more preferably less than 4 micrograms. It is additionally preferred that less than 10 micrograms of paclitaxel be released two days after implantation, more preferably less than 5 micrograms, and more preferably less than 2 micrograms.

FIG. 2 also demonstrates a continual release of drug over prolonged time frames. All curves in FIG. 2 show a relatively rapid release rate over the first few days, followed by a slower, sustained release over up to about two weeks. The inventors have found that such release rate characteristics are preferred for efficacy. In particular, the inventors have found that a coating system resulting in drug release for a period of at least eight days, and more preferably ten days, is preferred. Also, the inventors have found that the period of rapid release rate is most effective if the maximum release rate is achieved during 1-3 days after implantation, more preferably during the second day after implantation.

Although most examples herein use a polymeric carrier to deliver paclitaxel from a coated stent, it is anticipated that the optimal dosing and release rates identified by the inventors would apply to drug coated stent systems in which no polymer carrier is used, such as where paclitaxel or another drug is applied directly to the stent in the absence of a polymer carrier.

In still other embodiments, the stent is a degradable polymer stent that contains the paclitaxel, rather than being made from a biostable material that is coated with drug.

Although the invention is described as being specific to paclitaxel, it should be recognized that the inventors' findings should be applicable to a wide variety of drug systems.

What is claimed is:

1. A drug coated stent comprising:
   a structural member insertable into a body lumen of a patient; and
   a drug coated onto at least a portion of said structural member;
   wherein about 60 micrograms or less than 60 micrograms of the drug is released within ten days after insertion into the body lumen of the patient and
   the release rate is maximized between 24 hours and three days.

2. The drug coated stent of claim 1, wherein said drug comprises paclitaxel.

3. The drug coated stent of claim 1, wherein said drug is incorporated into a polymer carrier coated onto at least a portion of said structural member.

4. The drug coated stent of claim 3, wherein said polymer comprises styrene.

5. The paclitaxel coated stent of claim 2, wherein about 20 micrograms or less than 20 micrograms of paclitaxel is released from said stent ten days after exposure to an aqueous environment.

6. The paclitaxel coated stent of claim 2, wherein about 15 micrograms or less than 15 micrograms of paclitaxel is released from said stent ten days after exposure to an aqueous environment.

7. The paclitaxel coated stent of claim 2, wherein about 10 micrograms or less than 10 micrograms of paclitaxel is released from said stent ten days after exposure to an aqueous environment.

8. The paclitaxel coated stent of claim 2, wherein about 8 micrograms or less than 8 micrograms of paclitaxel is released from said stent ten days after exposure to an aqueous environment.

9. The paclitaxel coated stent of claim 2, wherein about 6 micrograms or less than 6 micrograms of paclitaxel is released from said stent ten days after exposure to an aqueous environment.

10. The paclitaxel coated stent of claim 2, wherein about 4 micrograms or less than 4 micrograms of paclitaxel is released from said stent ten days after exposure to an aqueous environment.

11. A paclitaxel coated stent comprising:

a structural member insertable into a body lumen of a patient; and paclitaxel coated onto at least a portion of said structural member;

wherein about 10 micrograms or less than 10 micrograms of paclitaxel is released from said stent two days after exposure to an aqueous environment and the release rate is maximized between 24 hours and three days.

12. The paclitaxel coated stent of claim 11, wherein about 5 micrograms or less than 5 micrograms of paclitaxel is released from said stent two days after exposure to an aqueous environment.

13. The paclitaxel coated stent of claim 11, wherein about 2 micrograms or less than 5 micrograms of paclitaxel is released from said stent two days after exposure to an aqueous environment.

* * * * *